United States Patent
Coopersmith et al.

(10) Patent No.: US 8,426,418 B2
(45) Date of Patent: Apr. 23, 2013

(54) METHOD TO TREAT MELANOMA IN BRAF INHIBITOR-RESISTANT SUBJECTS

(75) Inventors: Robert Coopersmith, Chestnut Hill, MA (US); Raphael Lehrer, Palo Alto, CA (US)

(73) Assignee: CollabRx Inc., Palo Alto, CA (US)

( * ) Notice: Subject to any disclaimer, the term of this patent is extended or adjusted under 35 U.S.C. 154(b) by 63 days.

(21) Appl. No.: 13/219,532

(22) Filed: Aug. 26, 2011

(65) Prior Publication Data

US 2012/0053185 A1 Mar. 1, 2012

Related U.S. Application Data

(60) Provisional application No. 61/377,853, filed on Aug. 27, 2010.

(51) Int. Cl.
  *A61K 31/506* (2006.01)
  *A61K 31/404* (2006.01)
  *A61K 31/44* (2006.01)
  *C12Q 1/48* (2006.01)
  *G01N 33/573* (2006.01)
  *A61P 35/00* (2006.01)

(52) U.S. Cl.
  USPC ...... 514/252.18; 514/275; 514/346; 514/414; 435/7.21; 435/15

(58) Field of Classification Search ............. 514/252.18, 514/275, 346, 414; 435/7.21, 15
  See application file for complete search history.

(56) References Cited

U.S. PATENT DOCUMENTS

| | | | |
|---|---|---|---|
| 5,792,783 | A | 8/1998 | Tang et al. |
| 6,573,293 | B2 | 6/2003 | Tang et al. |
| 6,894,051 | B1 | 5/2005 | Zimmermann et al. |
| 7,125,905 | B2 | 10/2006 | Tang et al. |
| 7,169,791 | B2 | 1/2007 | Breitenstein et al. |
| 7,211,600 | B2 | 5/2007 | Lipson et al. |
| 7,235,576 | B1 | 6/2007 | Riedl et al. |
| 2008/0003603 | A1 | 1/2008 | Holden et al. |
| 2009/0082313 | A1 | 3/2009 | Agoulnik et al. |

FOREIGN PATENT DOCUMENTS

WO  WO-2010/059742  5/2010

OTHER PUBLICATIONS

Davies et al., "Mutations of the BRAF Gene in Human Cancer," Nature (2002) 417:949-954.
Halaban et al., PLX4032, a Selective $BRAF^{V600E}$ Kinase Inhibitor, Activates the ERK Pathway and Enhances Cell Migration and Proliferation of $BRAF^{WT}$ Melanoma Cells, Pigment Cell Melanoma Res. (2010) 23(2):190-200.
International Search Report and Written Opinion for International Patent Application No. PCT/US2011/049432, mailed Jan. 20, 2012, 6 pages.
Shi et al., "Combinatorial Treatments that Overcome PDGFRβ-Driven Resistance of Melanoma Cells to $^{V600E}$ B-RAF Inhibition," Cancer Research (2011) 71:5067-5074.
Smalley, "Understanding Melanoma Signaling Networks as the Basis for Molecular Targeted Therapy," J. Invest. Dermatol. (published online 2009) 130(1):28-37.
International Preliminary Report on Patentability for PCT/US11/49432, mailed Sep. 27, 2012, 4 pages.

*Primary Examiner* — Raymond Henley, III
(74) *Attorney, Agent, or Firm* — Morrison & Foerster LLP

(57) ABSTRACT

Methods to treat cancer patients, especially melanoma patients, who have BRAF mutations and have become resistant to BRAF mutant kinase inhibitors employ inhibitors of multiple receptor tyrosine kinases. In addition, methods are described for identifying pharmaceutical compositions and drugs that will be successful in treating these patients.

12 Claims, No Drawings

METHOD TO TREAT MELANOMA IN BRAF INHIBITOR-RESISTANT SUBJECTS

CROSS-REFERENCE TO RELATED APPLICATION

This application claims priority from U.S. provisional application 61/377,853 filed 27 Aug. 2010. The contents of this document are incorporated herein by reference.

TECHNICAL FIELD

The in relates to methods to treat patients with melanoma, specifically those who have become resistant to B-Raf inhibitors. The treatments employ multikinase inhibitors, especially those that inhibit receptors for VEGF, PDGF, IGF and FGF.

BACKGROUND ART

It has been reported by Davies, H., et al., *Nature* (2002) 417:949-954 that BRAF somatic missense mutations occur in 66% of malignant melanomas as well as at lower frequencies in other cancers. The mutations are in the kinase domain and a single substitution (V599E, now corrected to V600E) accounts for 80% of these mutations. These mutations result in proteins that have increased kinase activity. As these mutations are associated with malignant melanoma, inhibitors of the BRAF kinase proteins resulting from the V600E mutation have been employed as chemotherapeutic agents. Among these is Plexxikon 4032 (PLX-4032), also known as RG7204 and as Zelboraf®. In one study, this inhibitor produced a 70% response rate in metastatic melanoma for patients with the mutation, but generally does not produce durable responses. That is, the patients become resistant to this inhibitor.

To date, there appear to be no treatments available that overcome the resistance acquired by these patients to the inhibitors of kinase activity in BRAF kinase protein.

Inhibitors of receptor tyrosine kinases, in general, have been used as therapeutic agents for treating cancers. For example, U.S. Pat. No. 6,573,293 describes and claims the use of such inhibitors, including the drug marketed as Sutent® for the treatment of cancers including melanoma. Similar compounds are also claimed as useful in treating gastrointestinal stromal tumors and allergy-associated conditions in U.S. Pat. No. 7,211,600.

Sutent® itself, which is the maleate salt of 5-(5-fluoro-2-oxo-1,2-dihydroindol-3-ylidenemethyl)-2,4-dimethyl-1H-pyrrole-3-carboxylic acid (2-diethylaminoethyl)amide is described and claimed in U.S. Pat. No. 7,125,905. Another such available drug is Nexavar® described and claimed in U.S. Pat. No. 7,235,576.

Applicants are aware of no suggestion in the art that these compounds are specifically effective in treating patients who have acquired resistance to BRAF mutant kinase inhibitors.

DISCLOSURE OF THE INVENTION

It has now been found that patients with cancer, especially melanoma, who have BRAF mutations and have become resistant to BRAF kinase inhibitors respond favorably to therapeutic agents that are general tyrosine kinase inhibitors, in particular those that inhibit tyrosine kinases associated with VEGF, PDGF, IGF or FGF receptors. Among these drugs are two that are currently available clinically, Sutent® and Nexavar®. Other candidate drugs may be evaluated using assay methods for tyrosine kinase inhibitors in general.

Thus, in one aspect, the invention is related to a method to treat cancer, especially malignant melanoma in a subject who is characterized by a BRAF mutation, and who has previously been treated with at least one BRAF inhibitor and become resistant thereto. The method comprises administering to said subject an effective amount of a receptor tyrosine kinase inhibitor.

In another aspect, the invention is directed to a method to identify candidate drugs that will be effective in treating these patients which method comprises ascertaining the ability of a test compound to inhibit tyrosine kinase associated with a spectrum of receptors. Successful candidates will inhibit these kinase activities.

MODES OF CARRYING OUT THE INVENTION

The invention relies on identifying those cancer patients who have acquired resistance to drugs that are inhibitors of the kinase encoded by the mutated BRAF gene. In some embodiments, this identification is part of the invention.

BRaf is a member of the Raf kinase family of serine/threonine-specific protein kinases. This protein plays a role in regulating the MAP kinase/ERKs signaling pathway, which affects cell division, differentiation, and secretion. A number of mutations in BRAF are known. In particular, the V600E mutation is prominent. Other mutations which have been found are R461I, I462S, G463E, G463V, G465A, G465E, G465V, G468A, G468E, N580S, E585K, D593V, F594L, G595R, L596V, T598I, V599D, V599E, V599K, V599R, K600E, A727V, and most of these mutations are clustered to two regions: the glycine-rich P loop of the N lobe and the activation segment and flanking regions.

Accordingly, to carry out the invention, a subject is first identified who has a BRAF mutation, has been treated with BRAF inhibiting drugs and has been monitored to ascertain that continued treatment with such drugs is no longer effective. Such inhibitors are known in the art and are designated as such by their supplier. There are several BRAF inhibitors known currently, including, besides PDC-4032, GSK2118436, and PLX-3603 (also known as R05212054). No doubt others will be developed in the future. The patient is monitored for response to this treatment.

Thus, the invention is directed to the treatment of a clearly identified patient population is one that has undergone a regimen involving BRAF inhibitors, but is not responding according to standard criteria. The standard criteria for resistance, for example, are Response Evaluation Criteria In Solid Tumors (RECIST) criteria, published by an international consortium including NCI.

Cancers that contain B-RAF mutations include non-Hodgkin lymphoma, colorectal cancer, malignant melanoma, papillary thyroid carcinoma, non-small cell lung carcinoma, and adenocarcinoma of lung.

Patients particularly benefitting are those that have progressive disease. Progressive disease is defined as at least a 20% increase in the sum of the largest diameter of target lesions, taking as reference the smallest sum of the largest diameter recorded since the treatment started or the appearance of one or more new lesions.

Those with stable disease will also benefit. Stable disease is defined as neither sufficient shrinkage to qualify for partial response nor sufficient increase to qualify for progressive disease, taking as reference the smallest sum of the largest diameter since the treatment started.

Once the patient population is identified, a suitable receptor tyrosine kinase inhibitor is selected. Combinations of such tyrosine kinase receptor inhibitors may also be used. Among currently available drugs that serve this function are Sutent® (sunitinib malate, U.S. Pat. No. 7,125,905), Nexavar® (sorafenib tosylate, U.S. Pat. No. 7,235,576), Gleevec® (imatinib mesylate, U.S. Pat. No. 6,894,051), and Tasigna® (nilotinib hydrochloride monohydrate, U.S. Pat. No. 7,169,791), all incorporated herein by reference. Others are under development.

Exemplary structures are:

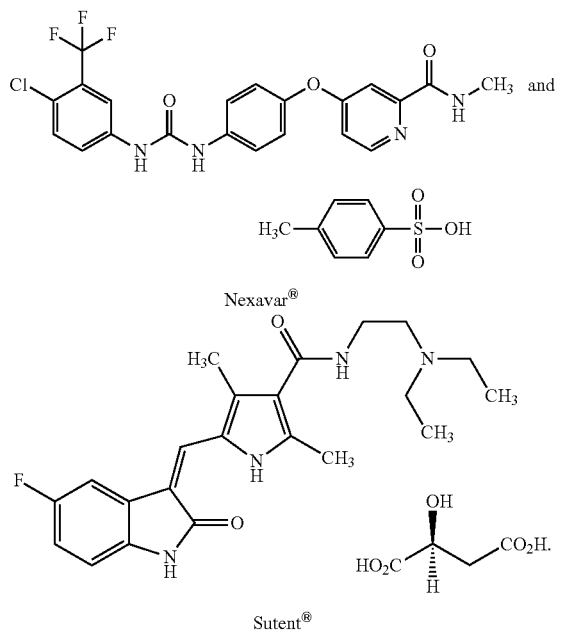

These drugs are characterized by their ability to inhibit tyrosine kinase activity associated with a spectrum of receptors. Additional candidate drugs are identified by testing the ability of a test compound to inhibit the tyrosine kinase activity of at least one receptor, preferably two receptors, more preferably three receptors and more preferably four or more receptors, such as the VEGF receptor, the FLK-1 receptor, the EGF receptor, the EGF-HER2 chimeric receptor, the HER2 receptor, the IGF-1 receptor, PDGF receptors, and insulin receptors. This is not an exhaustive list, and other receptors which respond to their ligands using a step that phosphorylates tyrosine may also be used as criteria for identifying suitable inhibitors.

Methods to assess the ability of test compounds to inhibit the tyrosine kinase activity of these receptors are well known in the art and several are illustrated in U.S. Pat. No. 5,792,783. Exemplified therein are ELISA assays modeled, according to the disclosure, after standard ELISA assays set forth in standard manuals for assessment of tyrosine kinase activity.

Typically, one set of useful assays relies on treating appropriate cells, such as NIH3T3 cells that have been altered recombinantly or which natively produce the desired receptor with the ligand for the receptor in the presence and absence of candidate compound, using these cells not treated with the ligand as a negative control. After incubation with the ligand and with the test compound either present at various dilutions or absent, extracts of the cells are added to ELISA plates on which an antibody specific for the receptor have been plated. Detection of phosphorylated tyrosine is then accomplished by treatment with antibodies specific for phosphorylated tyrosine and these antibodies detected by any suitable method, for example, by binding to fluorescent labeled or enzymatically labeled antibodies that immunoreact with the antibodies of the species from which the anti-phosphorylated tyrosine antibodies are derived. Further details of such assays are unnecessary since a multiplicity of variants of such assays is already known in the art. The specific methods used to detect the ability of compounds to inhibit the tyrosine kinase activity of a selected receptor are known in the art and do not themselves constitute a part of the invention. The invention is simply directed to a method to identify compounds that will be useful in treating the class of patients that have become resistant to inhibitors of the mutated BRAF kinase.

It will be apparent that suitable test compounds include those that are related to the above-described, currently approved drugs, and analogs to these structures would be suitable candidates for testing. Analogs of these structures are described in the above-referenced U.S. patents.

Successful candidates as determined in vitro may also be tested in laboratory animals. Thus, the method of the invention for use in treating patients who have acquired resistance to inhibitors of BRAF mutations, in particular the V600E mutation, may be tested in suitable animal models which may be murine, rabbit, rat, or other suitable model systems.

The selected drug or combination is administered in accordance with the judgment of the treating practitioner and in accordance with the labeling requirements. Dosage levels are those appropriate for the subject in question, and a variety of regimens for supplying the receptor tyrosine kinase inhibitors may be employed.

The kinase inhibitors useful in the invention can be formulated in a variety of compositions depending on the mode of administration. The formulation of such drugs is known in the art, and summarized, for example, in *Remington's Pharmaceutical Sciences*, latest edition, Mack Publishing Co., Easton, Pa., incorporated herein by reference.

The receptor tyrosine kinase inhibitors thus may be administered parenterally or through the digestive system, including oral administration. Parenteral delivery generally includes injection such as, for example, intravenous, subcutaneous, intramuscular, and intraperitoneal. The formulations may result in transmucosal or transdermal delivery as well, including intranasal and buccal delivery.

For treatment of solid tumors, localized delivery is also an option. Such delivery may be by injection, or may be topical, transmucosal, and the like. If the drugs are directed to treatment of melanoma, topical administration is a viable option.

For systemic parenteral delivery, a variety of physiologically acceptable carriers is available, including nanoparticulate formulations, liposomes, micelles, and the like. Such carriers can also be targeted using antibodies or fragments thereof specific for the targets, or by using receptor ligands. "Antibodies" includes all forms, including human and humanized antibodies as well as recombinantly produced single-chain antibodies and fragments.

Formulations for systemic administration by parenteral routes may include aqueous as well as lipophilic carriers. Similarly, formulations for administration, for example, by inhalation will include carriers that promote absorption across the nasal barrier and may be administered by aerosol spray using propellants such as trichlorofluoromethane, carbon dioxide or other propellant. The formulation to be administered may also be in the form of a powder or slurry.

In addition, the kinase inhibitors of the invention may be administered using sustained release formulations including implants. Such implants may be used proximal to any solid tumor or implanted within said tumor.

The kinase inhibitors of the invention, in particular those mentioned above, such as Sutent®, Nexavar®, Gleevec® and Tasigna® may be administered orally as capsules or tablets. Other forms of oral administration include syrups and gels as well as liquids. Typically, tablets and pills require a solid carrier and may be granulated and pressed into suitable shapes. Carriers such as sugars, starches, hydroxypropylmethylcellulose and polyvinyl pyrrolidone including mixtures thereof may be used.

In general, the mode of administration will depend on the nature of the drug and the nature of the tumor to be treated.

The dosage of the receptor kinase inhibitors of the invention is also dependent on the judgment of the practitioner, the mode of administration, the severity of the illness and a variety of factors known to the skilled artisan.

Optimization of dosage may be obtained through suitable clinical studies or animal models or both. In the case of approved drugs, formulations and dosages are set forth in labeling instructions; for example, Sutent® is provided in the form of capsules at 12.5 mg, 25 mg and 50 mg levels and dosages prescribed as 50 mg orally once daily with or without food for four weeks per treatment, but alternatives may also be practiced. Nexavar® is provided in the form of 200 mg tablets and instructions for typical dosages include two tablets orally twice daily without food. Gleevec® is supplied as an oral administration form as 100 mg or 400 mg tablets and Tasigna® in the form of 200 mg capsules. Adjustments of amount and route of administration may be made in light of the particular patient's condition.

As noted above, the pharmaceuticals useful in the invention are those that inhibit receptor tyrosine kinases of a spectrum of receptors. As also noted above, these include the receptors for VEGF, FGF, FLK, HER2, and the like. In general, inhibition of activity with a significant number of receptors is preferred.

Subsequent to the priority date herein, an article by Shi, H., et al., *Cancer Research* (2011) 71:5067-5074 was published that provides further support for the methods of the invention. According to this article, resistance to treatment with inhibitors of the kinase resulting from the $^{V600E}$B-RAF mutation is caused by upregulating the PDGFβ receptor. Phospho (p)-ERK and p-AKT are also upregulated. The article concluded that coordinating inhibition of the B-RAF mutated kinase with the RTK-PI3K-AKT-mTORC axis was effective in treatment.

All documents cited in the present specification are incorporated herein by reference.

The following examples are offered to illustrate but not to limit the invention.

EXAMPLE 1

A 55-year-old male had been on multiple lines of therapy, with a response to each, but then becoming resistant. The treatments were as follows:

| December 2007 | IL-2 treatment, 2 treatments |
|---|---|
| March-April 2008 | Interferon alpha-2b and CVD (cisplatin, vinblastine, and dacarbazine), 6 treatments |
| July 2009 | Carboplatin and Taxol ™ |
| November 2009 | Avastin ® |
| January 2010 | Plexxikon 4032 |

After the treatment with Plexxikon 4032, the patient's tumor shrank by 75% at the first scan, but in April 2010 second scan showed a recurrence. A GSK-MEK inhibitor was administered but it failed to produce a response. In July, ipilimumab (a therapy directed at CTLA-4, an inhibitor of the immune system) was started. Sutent® was then administered in addition to the ipilimumab. Within a few days, the patient's abdomen shrank to normal size and normal bowel movements resumed. As the patient, however, could not eat, he discontinued the Sutent® and died a few days after this discontinuation.

WO2010/059742 describes methods to formulate treatments for individual cancer patients by assessing genomic and/or phenotypic differences between cancer and normal tissues and integrating results to identify dysfunctional pathways. Application of these methods confirms the relevance of receptor kinase inhibitors to this particular patient.

The invention claimed is:

1. A method to treat a cancer in a subject bearing a BRAF mutation that enhances the kinase activity of the BRAF gene product, wherein said subject has become resistant to at least one BRAF kinase inhibitor, which method comprises administering to said subject an effective amount of an inhibitor effective against multiple receptor tyrosine kinases.

2. The method of claim 1 wherein the subject is human.

3. The method of claim 2 wherein the cancer is malignant melanoma.

4. The method of claim 2 wherein said BRAF mutation is a V600E mutation.

5. The method of claim 2 wherein said at least one BRAF inhibitor is Plexxikon 4032.

6. The method of claim 2 wherein the receptor tyrosine kinase inhibitor inhibits the receptor for VEGF, PDGF, IGF or FGF or combinations thereof.

7. The method of claim 2 wherein the receptor tyrosine kinase inhibitor is sunitinib malate, sorafenib tosylate, imatinib mesylate, or (nilotinib hydrochloride monohydrate or combination thereof.

8. The method of claim 2 wherein the receptor tyrosine kinase inhibitor is effective against at least three receptors.

9. A method to select a candidate compound for treatment of a subject who has become resistant to an inhibitor of the kinase resulting from a BRAF mutation which method comprises determining the ability of said candidate to inhibit tyrosine kinase activity associated with at least one receptor, wherein a candidate compound successful in said inhibition is a successful candidate for said treatment.

10. The method of claim 9 wherein said compound is successful in inhibiting the tyrosine kinase activity of at least two receptors.

11. The method of claim 9 wherein said compound is successful in inhibiting the tyrosine kinase activity of at least three receptors.

12. The method of claim 1 wherein the subject is a laboratory model for cancer.

* * * * *